US006459935B1

United States Patent
Piersma (10) Patent No.: US 6,459,935 B1
(45) Date of Patent: Oct. 1, 2002

(54) INTEGRATED FILTER FEED-THRU

(75) Inventor: Randall J. Piersma, Santa Clarita, CA (US)

(73) Assignee: AVX Corporation, Myrtle Beach, SC (US)

( * ) Notice: Subject to any disclaimer, the term of this patent is extended or adjusted under 35 U.S.C. 154(b) by 39 days.

(21) Appl. No.: 09/616,147

(22) Filed: Jul. 13, 2000

(51) Int. Cl.$^7$ .................... A61N 1/375; H01G 4/35
(52) U.S. Cl. ................... 607/37; 361/302
(58) Field of Search ............ 607/36–37; 128/901; 361/302, 306.1; 333/182, 184

(56) References Cited

U.S. PATENT DOCUMENTS

| | | | |
|---|---|---|---|
| 3,443,251 A | 5/1969 | Garstang et al. | |
| 3,920,888 A | 11/1975 | Barr | |
| 4,148,003 A | 4/1979 | Colburn et al. | |
| 4,152,540 A | 5/1979 | Duncan et al. | |
| 4,247,881 A | 1/1981 | Coleman | |
| 4,424,551 A | 1/1984 | Stevenson et al. | |
| 5,333,095 A | 7/1994 | Stevenson et al. | |
| 5,406,444 A | 4/1995 | Selfried et al. | |
| 5,531,003 A | 7/1996 | Seifried et al. | |
| 5,535,097 A | 7/1996 | Ruben et al. | |
| 5,620,476 A | 4/1997 | Truex et al. | |
| 5,650,759 A | 7/1997 | Hittman et al. | |
| 5,735,884 A | 4/1998 | Thompson et al. | |
| 5,751,539 A | 5/1998 | Stevenson et al. | |
| 5,759,197 A | 6/1998 | Sawchuk et al. | |
| 5,782,891 A | 7/1998 | Hassler et al. | |
| 5,817,130 A | * 10/1998 | Cox et al. | 607/5 |
| 5,825,608 A | 10/1998 | Duva et al. | |
| 5,836,992 A | 11/1998 | Thompson et al. | |
| 5,867,361 A | 2/1999 | Wolf et al. | |
| 5,870,272 A | 2/1999 | Seifried et al. | |
| 5,871,513 A | 2/1999 | Taylor et al. | |
| 5,896,267 A | 4/1999 | Hittman et al. | |
| 5,905,627 A | 5/1999 | Brendel et al. | |
| 5,959,829 A | * 9/1999 | Stevenson et al. | 361/302 |
| 5,999,398 A | * 12/1999 | Makl et al. | 361/302 |

OTHER PUBLICATIONS

Makl, Steve; "Passive Component Integration: An Array of Miniaturization Solutions"; 6 pages; in *Medical Electronics Manufacturing*, Fall 1996.

* cited by examiner

*Primary Examiner*—Kennedy Schaetzle
*Assistant Examiner*—Kristen Droesch
(74) *Attorney, Agent, or Firm*—Dority & Manning (57) ABSTRACT

A multi-leaded, filter feed-thru assembly for implantable medical devices, such as heart pacemakers, defibrillators, and neurostimulators, which integrates both multi-element semiconductor devices and passive component devices, or multi-element combinations thereof, together with a discoidal capacitive filter device to provide filtration of electromagnetic interference is provided. The assembly additionally provides for the suppression of high voltage transients from defibrillation and electrocautery procedures, as well as providing additional circuit and network functions.

49 Claims, 11 Drawing Sheets

INTEGRATED FILTER FEED-THRU

BACKGROUND OF THE INVENTION

The present invention generally relates to feed-thru capacitors of the type used in implantable medical devices such as heart pacemakers, defibrillators, and neurostimulators. More specifically, the instant invention relates to a multi-leaded feed-thru assembly combining a capacitive device and additional semi-conductive devices for use in implantable medical devices. Still further, the present invention relates to a multi-leaded feed-thru assembly which integrates both multi-element semiconductor devices and passive component devices, or multi-element combinations thereof, together with a discoidal capacitive filter device to provide filtration of electromagnetic interference (EMI).

Conventional feed-thru capacitive devices are known. In particular, ceramic capacitor feed-thru assemblies for use in implantable medical devices are known. With the continued miniaturization of electric devices and the desire for less invasive medical procedures, smaller multi-functional devices have become needed to increase the capabilities of implantable medical devices such as pacemakers while maintaining or even reducing their size and simultaneously increasing their reliability.

U.S. Pat. No. 5,735,884, issued to Thompson et al. and incorporated fully herein by reference, discloses a filtering feed-thru assembly for implantable medical devices. The '884 assembly, however, provides poor EMI filter performance due to the use of chip capacitors. While useful for its purpose, the absolute requirement for reliability of these implantable devices mandates that the feed-thru filter must be capable of filtering (i.e., reflecting or absorbing and decoupling) substantially all EMI to prevent damage to the device's internal circuitry. Failure of the implantable device could result in the loss of function of the medical device and possibly the loss of the patient's life.

U.S. Pat. Nos. 4,424,551 and 5,333,095, issued to Stevenson et al. and incorporated fully herein by reference, also disclose feed-thru filtering capacitive assemblies for use in medical devices. Neither of these assemblies, however, provides for the attachment of semiconductor or passive component devices to such filtering feed-thru devices. This results in an increase in medical device size due to the requirement for downstream assembly of such additional components into the internal circuitry of such a device, in addition to the associated increase in costs. Additionally, neither the '551 nor the '095 assembly provides for suppression of transient voltages at their point of entry (i.e., the end of the electrically conductive leads external to the implantable device).

It is, therefore, desirable to provide a multi-leaded feed-thru assembly capable of reliably and thoroughly filtering EMI, as well as, suppressing transient voltages at their point of entry into the implantable medical device and integrating both multi-element semiconductor devices and passive component devices, or multi-element combinations thereof, together with a discoidal capacitive filter.

SUMMARY OF THE INVENTION

The present invention recognizes and addresses various of the foregoing limitations and drawbacks, and others, concerning the filtration of electromagnetic interference, the suppression of transient voltages, and the integration of additional electronic components into a single assembly for implantable medical devices resulting in the reduction in size and increase in reliability of the medical device. Therefore, the present invention provides a new multi-leaded filtering feed-thru assembly for filtering EMI, such as may be generated by cellular telephones, and suppressing transient voltages, such as may be generated by a defibrillator, as well as allowing for the integration of additional electronic components into the assembly.

It is a principle object of the subject invention to provide a filtering feed-thru capacitive device. More particularly, it is an object of the present invention to provide a filtering feed-thru capacitive assembly capable of inclusion in an implantable medical device.

Another more particular object of the present invention is to provide a filtering feed-thru assembly capable of filtering EMI as may be experienced by an implanted medical device. In such context, it is a still further object of the present invention to provide a filtering feed-thru assembly capable of suppressing transient voltages as may be experienced by an implanted medical device.

It is a further general object of the present invention to provide a filtering feed-thru assembly capable of integration with both multi-element semiconductor devices and passive component devices, or multi-element combinations thereof. In such context, it is a still further object to provide a filtering feed-thru assembly comprising a discoidal capacitive filter.

It is a more specific object of the present invention to provide a filtering feed-thru assembly for an implantable medical device, capable of filtering electromagnetic interference from any external signals entering the device, suppressing any transient voltages at their entry point into the device, and capable of integration with both multi-element semiconductor and passive component devices, or multi-element combinations thereof, together with a discoidal capacitive filter.

Additional objects and advantages of the invention are set forth in, or will be apparent to those of ordinary skill in the art from, the detailed description as follows. Also, it should be further appreciated that modifications and variations to the specifically illustrated and discussed features and materials hereof may be practiced in various embodiments and uses of this invention without departing from the spirit and scope thereof, by virtue of present reference thereto. Such variations may include, but are not limited to, substitutions of equivalent means, features, and/or materials for those shown or discussed, and the functional or positional reversal of various parts, features, or the like.

Still further, it is to be understood that different embodiments, as well as different presently preferred embodiments, of this invention, may include various combinations or configurations of presently disclosed features, elements, or their equivalents (including combinations of features or configurations thereof not expressly shown in the figures or stated in the detailed description).

These and other features, aspects and advantages of the present invention will become better understood with reference to the following description and appended claims. The accompanying drawings, which are incorporated in and constitute a part of this specification, illustrate an embodiment of the invention and, together with the description, serve to explain the principles of the invention.

In one exemplary embodiment of the present invention the assembly comprises a feed-thru filter for a pacemaker or other implantable medical device. Such assembly may have a header, a support plate, with a flange around its outer perimeter for attachment in an opening in the housing of the implantable device. Such attachment can be achieved through any known means but is typically completed by welding or brazing and is preferably a hermetic sealing of the assembly within such opening in the device.

Within such header may be a single opening or set of openings through which extend multiple electrically conductive terminal pins. A first end of each of such pins remains external to the implantable medical device when such assembly is connected thereto. Preferably, the opening or set of openings in such header through which such pins pass is hermetically sealed. Within the opening or within each opening in a set of openings may be an electrically insulative support. Such supports, while aiding in sealing the opening or set of openings, may maintain the pins within the opening or set of openings and electrically insulate them from portions of the circuitry of such assembly and such medical device.

A discoidal capacitor may be bonded to such header by a conductive polyamide. Such discoidal capacitor may have a second set of openings formed therethrough. Such openings in the capacitor may align with the opening or set of openings through such header when the two are bonded together. This may allow for electrical connection between such discoidal capacitor and such electrically conductive terminal pins.

Within such discoidal capacitor may be a first set of electrode plates arranged to be suitable for parallel connections with such pins and a second set of electrode plates arranged to be suitable for series connections with such pins. Such parallel connections with the pins allow-for the filtering of a majority of any electromagnetic interference which may be experienced by such medical devices. Similarly, such series connections with the pins allow for suppression of transient voltage spikes as may be experienced by such implantable devices during defibrillation. In particular, direct current (DC) is reflected or blocked and alternating current (AC) is absorbed and decoupled by the series capacitive electrode plates.

On the opposing side of such discoidal capacitor from such header, electrically conductive patterns may be disposed for further connection to additional electronic component elements. Such patterns may also provide for connection to the internal circuitry of such medical device. This may be achieved through either the use of wire bondable pads integrated into such patterns or a second set of terminal pins connected to such discoidal capacitor. In the later instance, the first set of such terminal pins may be used for suppressing transient voltages while the second set may be utilized to filter EMI or vise versa.

Should such patterns be used for connection to an additional electrical component, such component may be a multi-element semiconductor and a passive component device, or a multi-element combination thereof. For example, such electrical component may be a semiconductor attached to such discoidal capacitor by solder reflow, a multi-element passive component attached by epoxy bonding and conductive polyamide, or a thick film resistor or inductor attached by firing.

One of ordinary skill in the art would recognize that any combination of additional electronic component, such discoidal capacitor, and connection type to the internal circuitry of such implantable devices is possible. Additionally, such terminal pins may be located in-line or on a bolt circle and such insulative supports may constitute either a single multi-hole support or individual supportive elements. Finally, such header may either provide only a supportive plate for the remainder of the assembly or may constitute a canister to contain the entire assembly.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Repeat use of reference characters throughout the present specification and appended drawings is intended to represent the same or analogous features or elements of the invention.

DETAILED DESCRIPTION OF THE PREFERRED EMBODIMENTS

Reference will now be made in detail to presently preferred embodiments of the invention, examples of which are fully represented in the accompanying drawings. Such examples are provided by way of an explanation of the invention, not limitation thereof In fact, it will be apparent to those skilled in the art that various modifications and variations can be made in the present invention, without departing from the spirit and scope thereof. For instance, features illustrated or described as part of one embodiment can be used on another embodiment to yield a still further embodiment. Still further, variations in selection of materials and/or characteristics may be practiced, to satisfy particular desired user criteria. Thus, it is intended that the present invention cover such modifications and variations as come within the scope of the present features and their equivalents.

Figure 1:
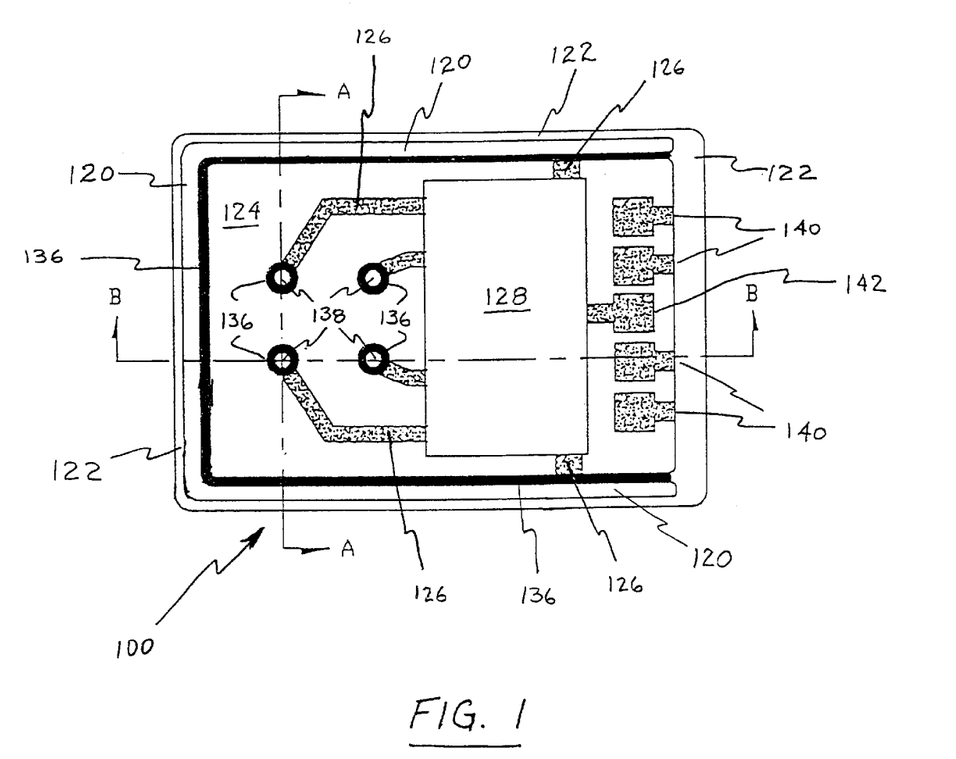
FIG. 1 is an overhead perspective view of an exemplary embodiment of the present invention illustrating a filtering feed-thru assembly with electrically conductive pins located on a bolt circle and wire bondable pads for connection to a circuit and to ground.

As disclosed above, the present invention is particularly concerned with a multi-leaded feed-thru filter assembly capable of reliably and thoroughly filtering EMI, as well as, suppressing transient voltages and integrating both multi-element semiconductor devices and passive component devices, or multi-element combinations thereof, together with a discoidal capacitor. FIG. 1 depicts a first preferred embodiment of the present invention including an exemplary filtering feed-thru assembly 100 having a header 120, a three-sided canister, with a flange 122 around its outer perimeter for attachment in an opening in the housing of the implantable device (not shown).

Disposed upon the header 120 is an exemplary discoidal capacitor 124. On the upper surface of the discoidal capacitor 124 is an electrically conductive pattern 126 to be discussed in detail later. In electrical communication with the pattern 126 is an electronic component 128. In accordance with the first embodiment this additional electronic component 128 may be a semiconductor attached to such discoidal capacitor 124 by solder reflow, a multi-element passive component attached by epoxy bonding and conductive polyamide, or a thick film resistor or inductor attached by firing.

Figure 3:
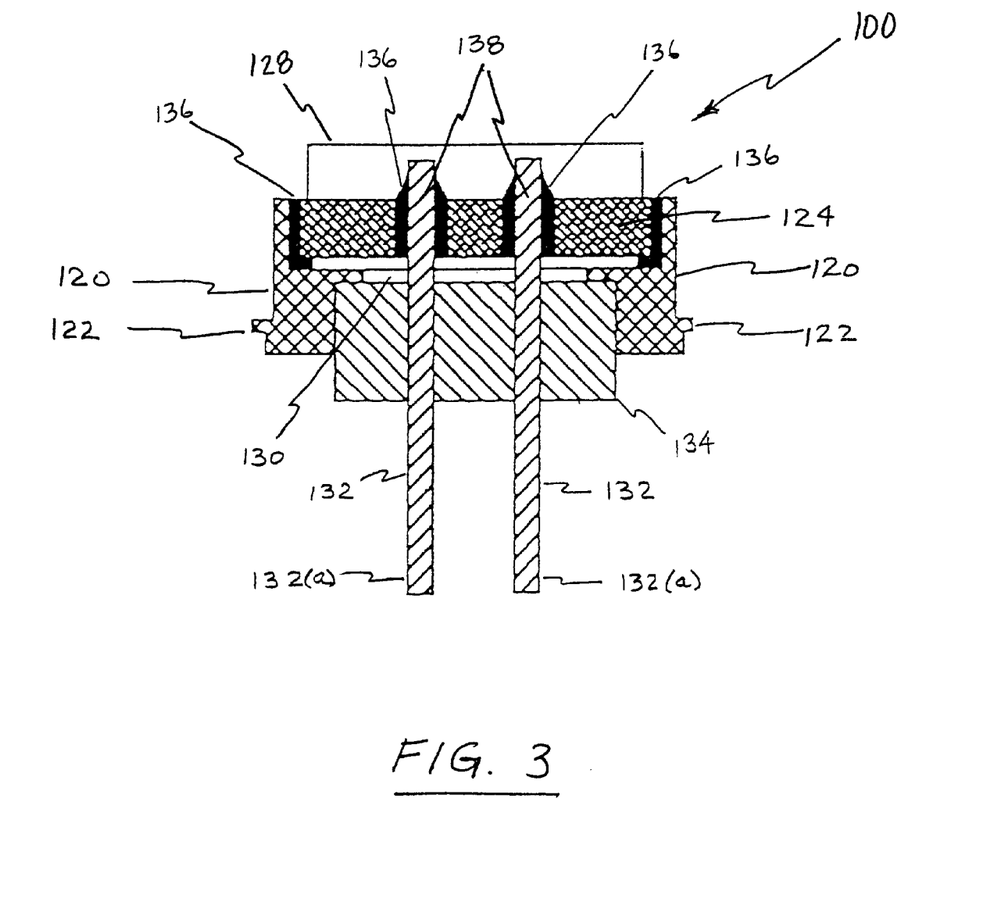
FIG. 3 is a cross-sectional view of the exemplary embodiment of FIG. 1 taken along line A—A showing at least two of the electrically conductive pins extending through the header and supported by an electrically insulative support, as well as an exemplary discoidal capacitor and an additional electronic component.
Figure 4:
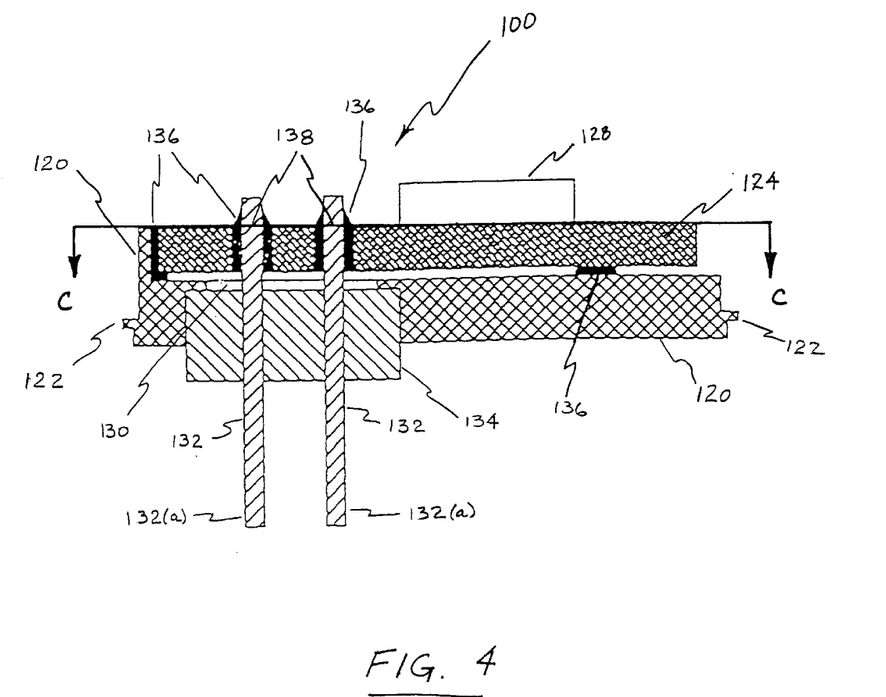
FIG. 4 is a cross-sectional view of the exemplary embodiment of FIG. 1 taken along line B—B showing at least two of the electrically conductive pins extending through the header (shown to be a canister) and supported by an electrically insulative support, as well as an exemplary discoidal capacitor and an additional electronic component connected via a conductive polyamide.

As best seen in FIGS. 3 and 4, the header 120 is a supportive surface for the remainder of the assembly 100. The header has an opening 130 through which pass a corresponding set of terminal pins 132. Each terminal pin 132 has a respective first 132(a) and second end opposite the first end thereof. The first end 132(a) of each terminal pin remains external to the implantable device (not shown) when the assembly 100 is connected thereto. The terminal pins 132 are maintained in the opening 130 by an exemplary electrically insulative support 134. The support 134 may be either a single multi-hole support or a set of individual supports in an embodiment where a set of individual openings exists in the header 120.

In accordance with the present embodiment, the exemplary discoidal capacitor 124 is bonded to the supportive surface of the header 120 with a conductive polyamide 136. The capacitor 124 has a set of openings 138 disposed therethrough, in the present embodiment arranged in a bolt circle, for passage of the terminal pins 132. The set of openings 138 in the discoidal capacitor are aligned with the opening 130 in the header 120 to allow for passage of the terminal pins 132 through the bonded pair. Within the set of openings 138 in the discoidal capacitor 124, the terminal pins 132 are maintained in electrical communication by use of the same conductive polyamide 136 used to bond the header 120 and the discoidal capacitor 124.

Within the exemplary discoidal capacitor 124 is a first set of electrode plates (not shown) arranged to be in parallel connection with the terminal pins 132 and a second set of electrode plates (not shown) arranged to be in series connection with the terminal pins 132. The electrode plates are diagrammatically represented by the arrangement of FIG. 2, and those of ordinary skill in the art will understand the details thereof without additional discussion, which details form no particular aspect of the subject invention beyond the disclosure herewith. Such parallel connections with the pins 132 allow for the filtering of a majority of any electromagnetic interference which may be experienced by such medical devices. Similarly, such series connections with the pins 132 allow for suppression of transient voltage spikes as may be experienced by such implantable devices during defibrillation. To be more specific, direct current (DC) transients are reflected away or blocked from the device while alternating current (AC) transients are absorbed and decoupled by the series capacitive electrode plates.

Figure 2:
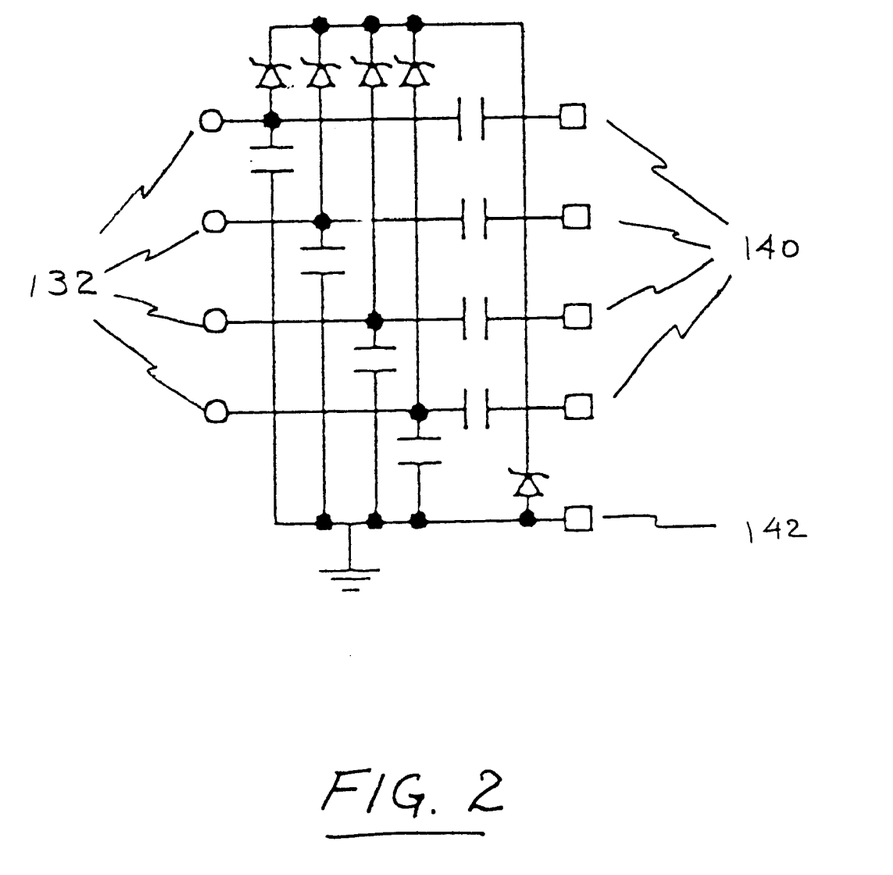
FIG. 2 is a schematic diagram of the exemplary embodiment of FIG. 1 showing parallel capacitors for filtering electromagnetic interference and series capacitors for suppressing transient voltages.
Figure 5:
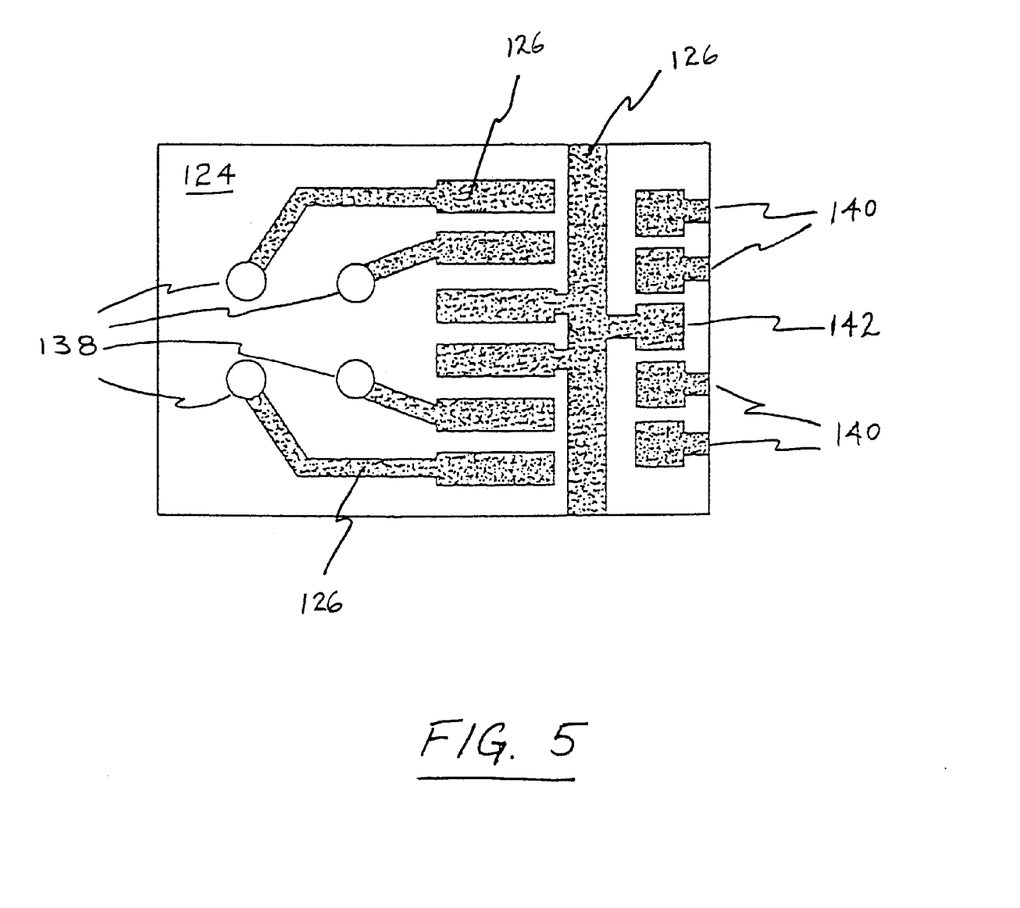
FIG. 5 is an overhead perspective view of the exemplary embodiment of FIG. 1 taken along line C—C of FIG. 4 showing an exemplary electrically conductive pattern on the upper surface of the discoidal capacitor connecting the electrically conductive pins, the additional electronic component, and the wire bondable pads.

As shown in FIGS. 1 and 5, on the opposing side of the discoidal capacitor 124 from the header 120, an exemplary electrically conductive pattern 126 is disclosed for connection of additional electronic components. The disclosed pattern 126 also provides for connection to the internal circuitry of the medical device. In the present embodiment this is achieved through the use of wire bondable pads 140 integrated into the pattern 126. Notably, the center wire bondable pad 142 preferably is a ground. FIG. 2 depicts a schematic diagram of the assembly 100 including the terminal pins 132, the parallel and series capacitive electrode plates and the wire bonded pads 140 and 142 on the upper surface of the discoidal capacitor 124.

Figure 6:
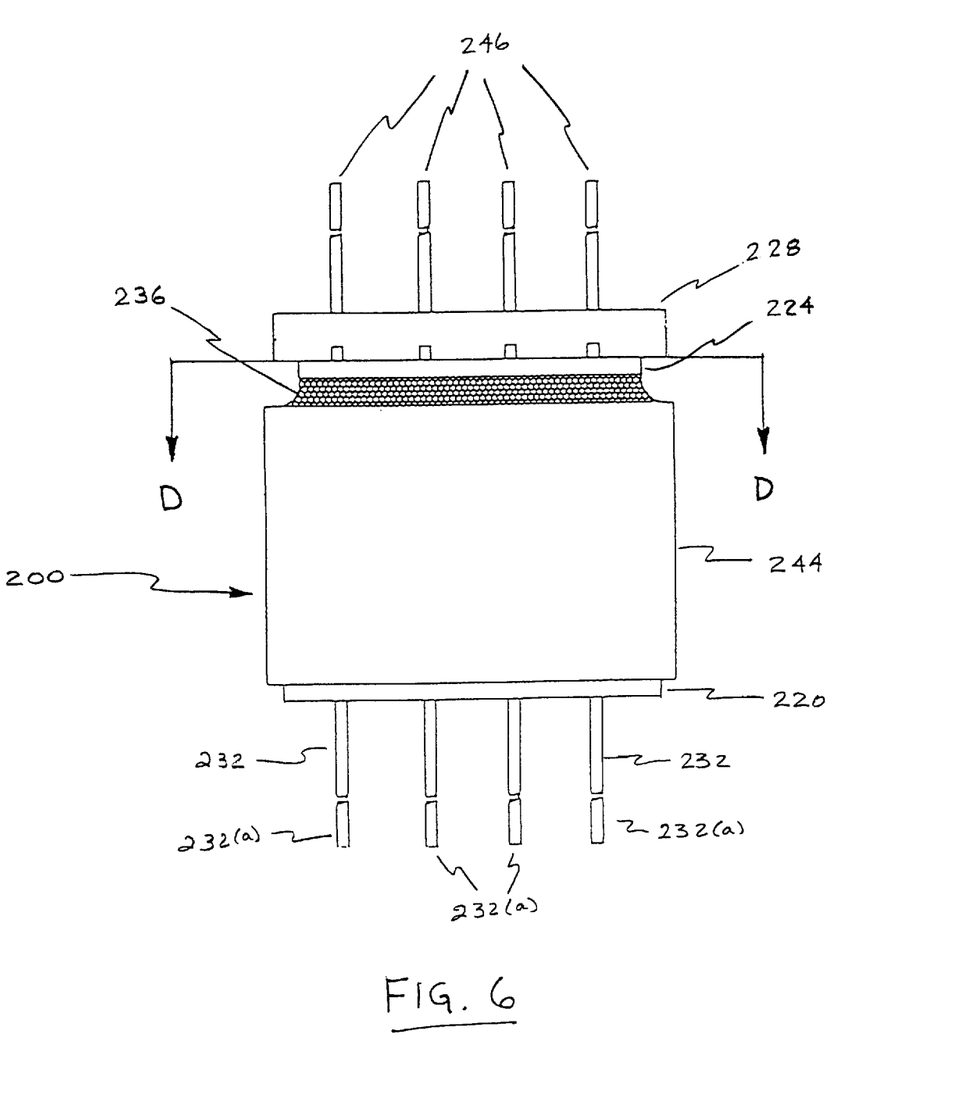
FIG. 6 is a perspective side view of a second exemplary embodiment of the present invention illustrating a filtering feed-thru assembly with a first set of electrically conductive pins located in-line and a second set of electrically conductive pins for connection to the internal circuitry of the implantable medical device.
Figure 7:
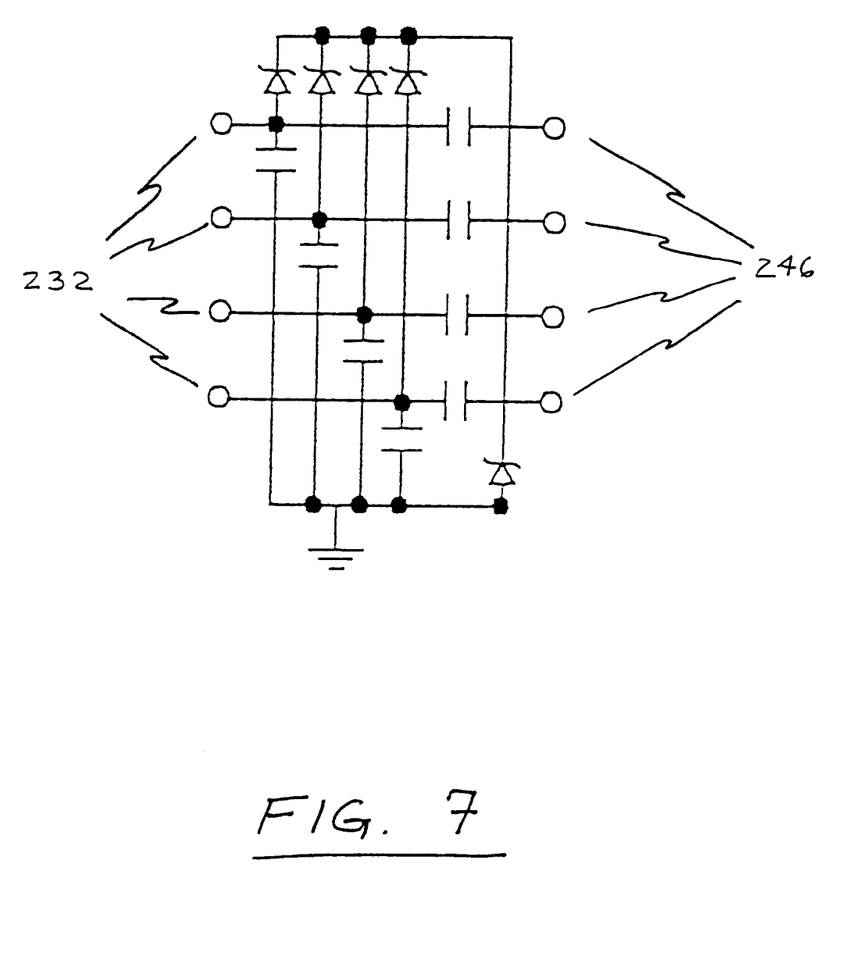
FIG. 7 is a schematic diagram of the exemplary embodiment of FIG. 6 showing parallel capacitors for filtering electromagnetic interference and series capacitors for suppressing transient voltages.
Figure 8:
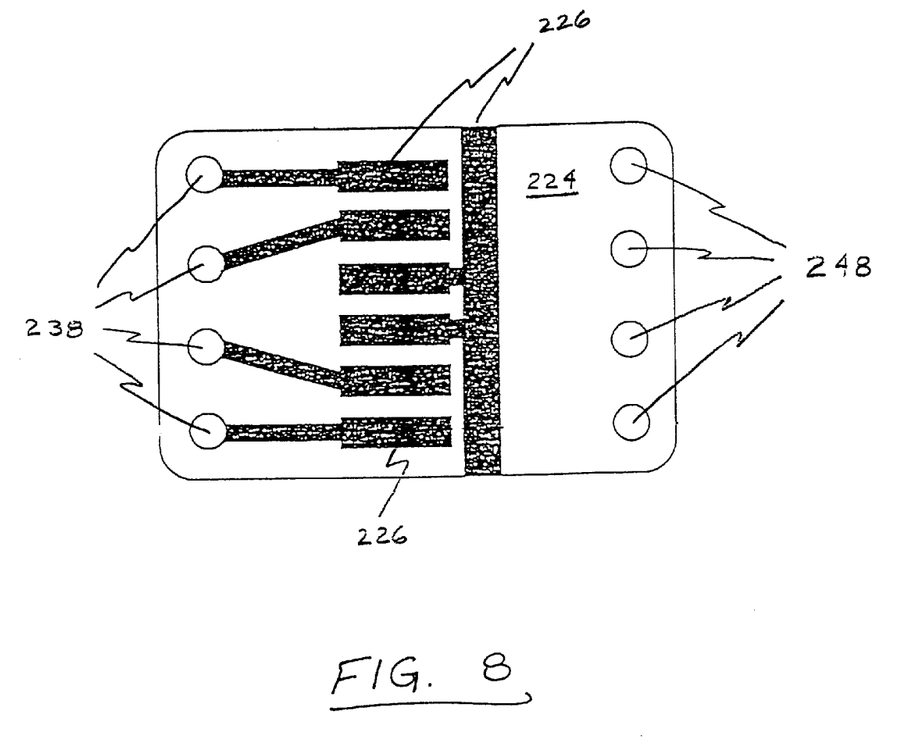
FIG. 8 is an overhead perspective view of the exemplary embodiment of FIG. 6 taken along line D—D of FIG. 6 showing an exemplary electrically conductive pattern on the upper surface of the discoidal capacitor connecting a first set of the in-line electrically conductive pins and the additional electronic component and the second set of in-line electrically conductive pins for connection to the internal circuitry of the implantable device.

In a second exemplary preferred embodiment of the present invention, as shown in FIGS. 6–8, an additional capacitive device 244 has been placed between the header 220 and the discoidal capacitor 224. The method of bonding, a conductive polyamide 236, is identical to that previously described. This additional capacitor 244 has a first set of electrode plates arranged to be in parallel connection with the first set of preferably in-line terminal pins 232 and a second set of electrode plates arranged to be in series connection with the pins 232. The addition of another capacitive device 244 capable of both filtering EMI and suppressing transient voltages aids in the reliability of the device.

As in the previous embodiment, an electrically conductive pattern 226 is disposed on the upper surface of the discoidal capacitor 224 allowing for the connection of an additional electronic component 228 to the assembly 200. In the present preferred embodiment, however, the discoidal capacitor 224 has two sets of openings therethrough. See, for example, FIG. 8. The first set of openings 238 is identical in form and purpose as that disclosed in the prior embodiment. The second set of openings 248 is for passage of an second set of terminal pins 246 through the discoidal capacitor. This second set of pins 246 replaces the wire bonded pads 140 and 142 of the first preferred embodiment as can be seen in the schematic diagram of FIG. 7.

Figure 9:
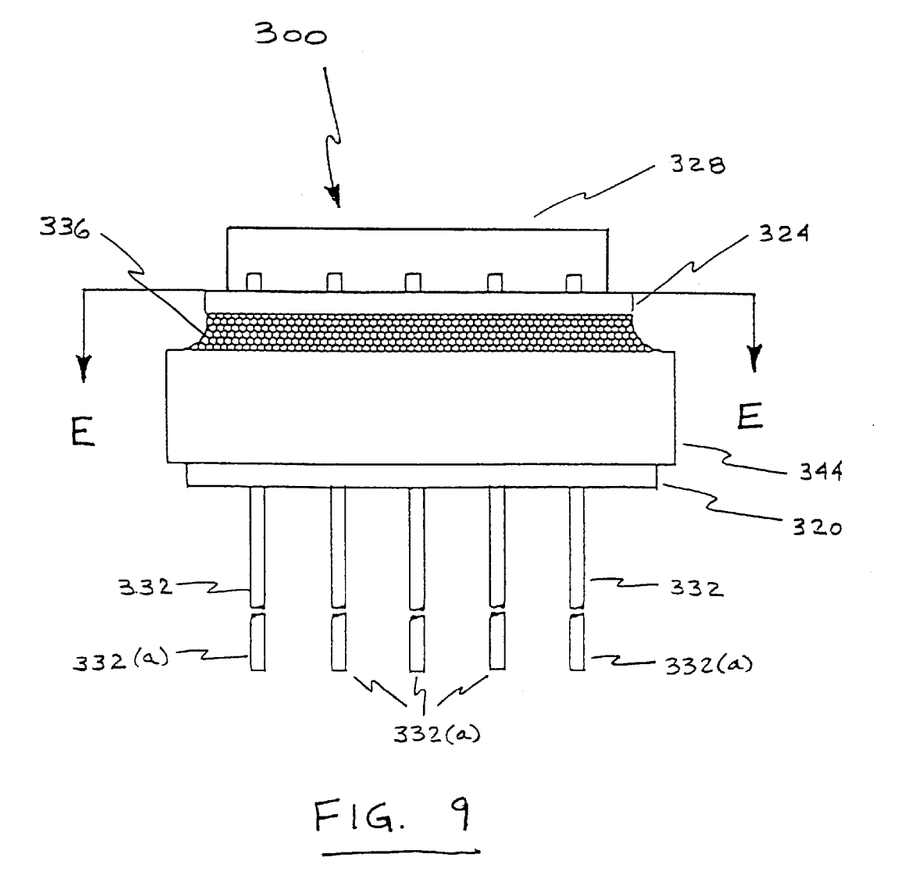
FIG. 9 is a side perspective view of a third exemplary embodiment of the present invention illustrating a filtering feed-thru assembly with electrically conductive pins located in-line and wire bondable pads for connection to internal circuitry of an implantable medical device.
Figure 10:
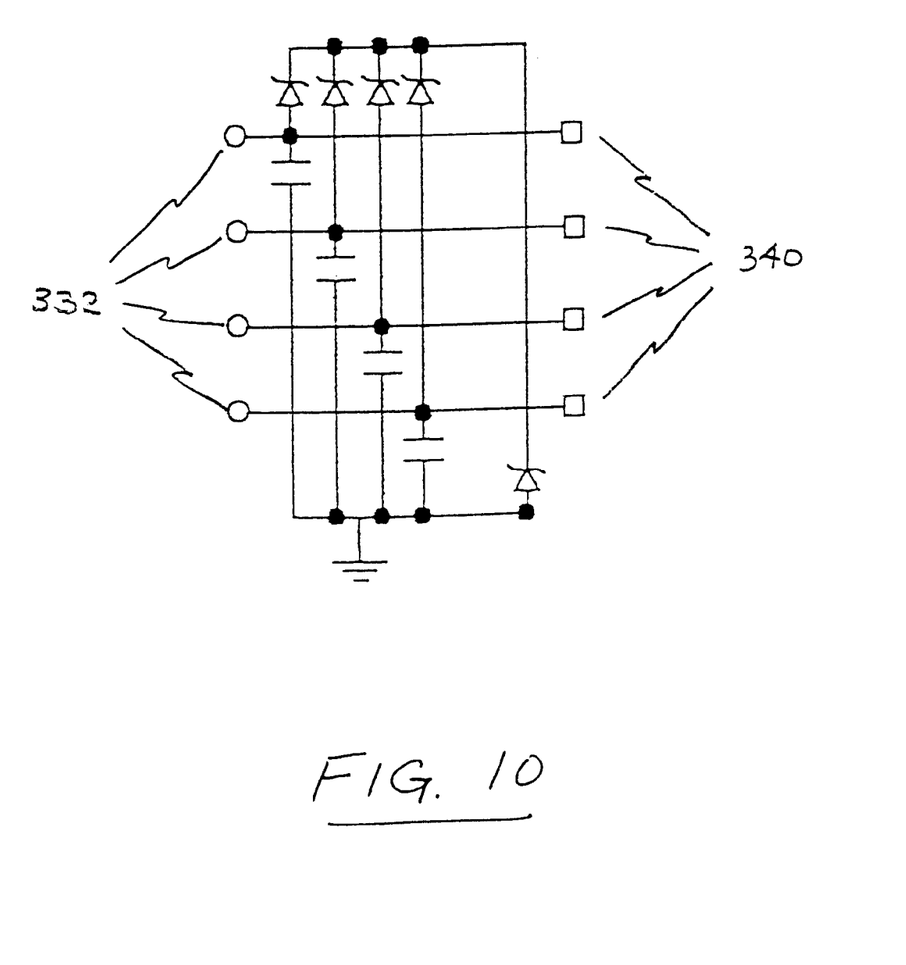
FIG. 10 is a schematic diagram of the exemplary embodiment of FIG. 9 showing parallel capacitors for filtering electromagnetic interference.
Figure 11:
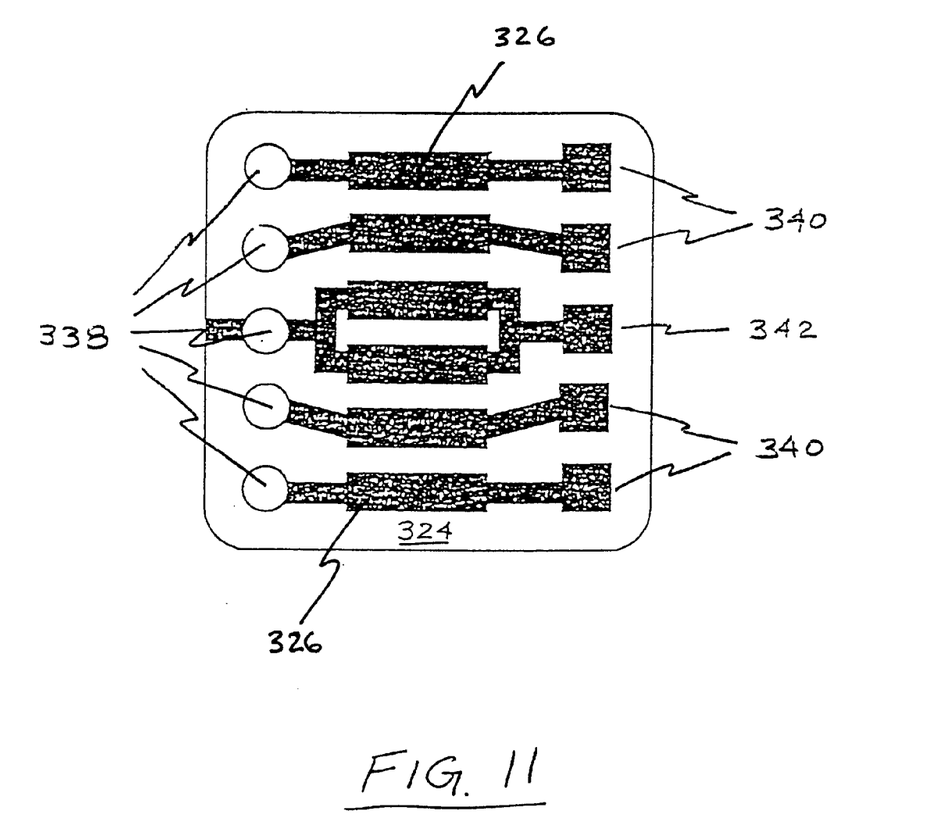
FIG. 11 is an overhead perspective view of the exemplary embodiment of FIG. 9 taken along line E—E of FIG. 9 showing an exemplary electrically conductive pattern on the upper surface of the discoidal capacitor connecting the in-line electrically conductive pins, the additional electronic component, and the wire bondable pads.

In a third exemplary preferred embodiment of the present invention, as seen in FIGS. 9–11, an additional capacitive device 344 has been placed between the header 320 and the discoidal capacitor 324. The method of bonding, a conductive polyamide 336, is identical to that previously described. This additional capacitor 344 has a set of electrode plates arranged to be in parallel connection with the in-line terminal pins 332. In this embodiment, there are no series connections with the pins 332 which allows for a thinner assembly 300 and reduced production costs. The absence of the series capacitors can clearly be seen in the schematic diagram of the assembly as shown in FIG. 10.

As seen in FIG. 11, an electrically conductive pattern 326 is disposed on the upper surface of the discoidal capacitor 324 allowing for the connection of an additional electronic component 328 to the assembly 300. In the present preferred embodiment, the disclosed pattern 326 also provides for connection to the internal circuitry of the medical device through the use of wire bondable pads 340 integrated into the pattern 326.

Although several preferred embodiments of the invention have been described using specific terms and devices, such descriptions are for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of various other embodiments may be interchanged both in whole or in part. Therefore, the spirit and scope of the appended claims should not be limited to the description of the preferred versions contained herein.

What is claimed is:

1. A filtered feed-thru assembly for implantable medical devices, the assembly comprising:
   (a) a header having a supportive surface with a flange on the outer perimeter thereof for attachment to an implantable housing and a first opening defined through said header;
   (b) multiple electrically conductive terminal pins disposed within and extending through said first opening, said terminal pins each having respective first and second ends;
   (c) an electrically insulative support for said multiple electrically conductive terminal pins, said electrically insulative support being disposed within said first opening;
   (d) a discoidal capacitive device with an upper and lower side, said lower side connected to said support surface of said header, comprising a first set of electrode plates arranged to be suitable for parallel connections with said multiple electrically conductive terminal pins, a second set of electrode plates arranged to be suitable for series connections with said multiple electrically conductive terminal pins, and a second set of openings defined through said discoidal capacitive device for passage of said terminal pins, wherein said first opening through said header aligns with said second set of openings in said discoidal capacitive device when they are bonded; and
   (e) wherein electrically conductive patterns are disposed on said upper side of said discoidal capacitor and an electrical component is connected to said electrically conductive patterns.

2. The assembly of claim 1, wherein said electrically insulative supports comprise a single multi-hole insulator.

3. The assembly of claim 1, wherein said multiple electrically conductive terminal pins are in-line.

4. The assembly of claim 1, wherein said multiple electrically conductive terminal pins are on a bolt circle.

5. The assembly of claim 1, wherein said supportive surface comprises a canister.

6. The assembly of claim 1, wherein said lower side of said discoidal capacitive device is bonded to said supportive surface by a nonconductive bonding and electrical connections are made by means of conductive polymers.

7. The assembly of claim 6, wherein said electrically conductive patterns included wire bondable pads for connection to circuitry in said implantable housing.

8. The assembly of claim 6, wherein said electrical component is a semiconductor and is attached to said upper side of said discoidal capacitive device by solder reflow.

9. The assembly of claim 6, wherein said electrical component is a multi-element passive component attached to said upper side of said discoidal capacitive device by epoxy bonding and conductive polyamide.

10. The assembly of claim 6, wherein said electrical component is a thick film resistor attached to said upper side of said discoidal capacitive device by firing.

11. The assembly of claim 6, wherein said electrical component is an inductor attached to said upper side of said discoidal capacitive device by firing.

12. The assembly of claim 1, wherein said header forms a portion of an outer surface of said implantable medical device.

13. The assembly of claim 12, wherein said header is connected to said implantable housing by welding.

14. The assembly of claim 12, wherein said header is connected to said implantable housing by brazing.

15. The assembly of claim 12, wherein said assembly is hermetically sealed within said implantable housing.

16. The assembly of claim 12, wherein said multiple electrically conductive terminal pins are hermetically sealed in said first opening through said header.

17. The assembly of claim 16, wherein said first ends of said multiple electrically conductive pins are external to said implantable housing.

18. A filtered feed-thru assembly for implantable medical devices, the assembly comprising:
   (a) a header with a flange around the outer perimeter thereof for attachment to an implantable housing and a first set of openings through said header;
   (b) electrically conductive pins disposed within and extending through said first set of openings, each of said pins having respective first and second ends;
   (c) a discoidal capacitive device with an upper and lower surface, said device connected to said header, said device further comprising a first set of electrode plates arranged to be suitable for electrical parallel connections with said electrically conductive pins and a second set of electrode plates arranged to be suitable for electrical series connections with said electrically conductive pins, a second set of openings formed therethrough for passage of said pins, wherein said first set of openings in said header align with said second set of openings in said discoidal capacitive device when bonded, and wherein said electrical connections are made by means of conductive polymers; and
   (d) wherein electrically conductive patterns are disposed on said upper side of said discoidal capacitor and an electrical component connected to said electrically conductive patterns.

19. The assembly of claim 18, further comprising electrically insulative supports for said electrically conductive pins, said insulative supports being disposed within said first set of openings in said header.

20. The assembly of claim 19, wherein said electrically insulative supports comprise a single multi-hole insulator.

21. The assembly of claim 18, wherein said electrically conductive pins comprise terminal pins.

22. The assembly of claim 18, wherein said electrically conductive pins are in-line.

23. The assembly of claim 18, wherein said electrically conductive pins are on a bolt circle.

24. The assembly of claim 18, wherein said header comprises a canister.

25. The assembly of claim 18, wherein said header comprises a portion of an outer surface of said implantable medical device.

26. The assembly of claim 25, wherein said header is connected to said implantable housing by welding.

27. The assembly of claim 25, wherein said header is connected to said implantable housing by brazing.

28. The assembly of claim 25, wherein said assembly is hermetically sealed within an opening in said implantable housing.

29. The assembly of claim 25, wherein said electrically conductive pins are hermetically sealed in said first set of openings through said header.

30. The assembly of claim 29, wherein said first ends of said electrically conductive pins are external to said implantable housing.

31. The assembly of claim 18, wherein said lower side of said discoidal capacitive device is bonded to said header by a nonconductive bonding and wherein electrical connections are made by means of conductive polymers.

32. The assembly of claim 31, wherein said electrically conductive patterns included wire bondable pads for connection to circuitry in said implantable housing.

33. The assembly of claim 31, wherein said electrical component is a semiconductor and is attached to said upper side of said discoidal capacitive device by solder reflow.

34. The assembly of claim 31, wherein said electrical component is a multi-element passive component attached to said upper side of said discoidal capacitive device by epoxy bonding and conductive polyamide.

35. The assembly of claim 31, wherein said electrical component is a thick film resistor attached to said upper side of said discoidal capacitive device by firing.

36. The assembly of claim 31, wherein said electrical component is an inductor attached to said upper side of said discoidal capacitive device by firing.

37. A filtered feed-thru assembly for implantable medical devices, the assembly comprising:

(a) a header having a supportive surface with a flange around the outer perimeter thereof and a first set of openings defined through said header, said header forming a portion of an outer surface of an implantable housing;

(b) multiple electrically conductive terminal pins disposed within and extending through said first set of openings, said terminal pins each having respective first and second ends and being hermetically sealed within said first set of openings through said header;

(c) electrically insulative supports for said multiple electrically conductive terminal pins, said insulative supports being disposed within said first set of openings;

(d) a discoidal capacitive device with a lower side bonded to said supportive surface of said header by a nonconductive bonding with electrical connections made by means of conductive polymers and an upper side opposite said lower side, such that electrically conductive patterns including wire bondable pads for connection to circuitry in said implantable housing are provided, said discoidal capacitive device comprising a first set of electrodes arranged to be suitable for parallel connections with said multiple terminal pins, and a second set of electrodes arranged to be suitable for series connections with said multiple terminal pins, and said discoidal capacitive device having a second set of openings formed therethrough for passage of said terminal pins, wherein said first set of openings through said header align with said second set of openings in said discoidal capacitive device when they are bonded; and (e) an electrical component connected to said upper side of said discoidal capacitive device.

38. The assembly of claim 37, wherein said header is connected to said implantable housing by welding.

39. The assembly of claim 37, wherein said header is connected to said implantable housing by brazing.

40. The assembly of claim 37, wherein said assembly is hermetically sealed within said implantable housing.

41. The assembly of claim 40, wherein said first ends of said electrically conductive pins are external to said implantable housing.

42. The assembly of claim 37, wherein said electrically insulative supports comprise a single multi-hole insulator.

43. The assembly of claim 37, wherein said multiple electrically conductive terminal pins are in-line.

44. The assembly of claim 37, wherein said multiple electrically conductive terminal pins are on a bolt circle.

45. The assembly of claim 37, wherein said supportive surface is a canister.

46. The assembly of claim 37, wherein said electrical component is a semiconductor attached to said upper side of said discoidal capacitive device by solder reflow.

47. The assembly of claim 37, wherein said electrical component is a multi-element passive component attached to said upper side of said discoidal capacitive device by epoxy bonding and conductive polyamide.

48. The assembly of claim 37, wherein said electrical component is a thick film resistor attached to said upper side of said discoidal capacitive device by firing.

49. The assembly of claim 37, wherein said electrical component is an inductor attached to said upper side of said discoidal capacitive device by firing.

* * * * *